(12) United States Patent
Stone et al.

(10) Patent No.: US 9,398,906 B2
(45) Date of Patent: *Jul. 26, 2016

(54) METHOD AND APPARATUS FOR PASSING A SUTURE

(71) Applicant: Biomet Sports Medicine, LLC, Warsaw, IN (US)

(72) Inventors: Kevin T. Stone, Winona Lake, IN (US); Christopher Palese, South Whitley, IN (US); Mary Sinnott, Logan, UT (US); Darin Ewer, Providence, UT (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 131 days.

This patent is subject to a terminal disclaimer.

(21) Appl. No.: 14/221,870

(22) Filed: Mar. 21, 2014

(65) Prior Publication Data

US 2014/0207158 A1    Jul. 24, 2014

Related U.S. Application Data

(63) Continuation of application No. 13/114,483, filed on May 24, 2011, now Pat. No. 8,679,135.

(60) Provisional application No. 61/348,016, filed on May 25, 2010.

(51) Int. Cl.
*A61B 17/04* (2006.01)
*A61B 17/06* (2006.01)

(52) U.S. Cl.
CPC ......... *A61B 17/0482* (2013.01); *A61B 17/0469* (2013.01); *A61B 17/0485* (2013.01); *A61B 17/06109* (2013.01); *A61B 2017/047* (2013.01);

(Continued)

(58) Field of Classification Search
CPC .......... A61B 17/0469; A61B 17/0482; A61B 17/0485; A61B 2017/047; A61B 2017/06052; A61B 2017/06076; A61B 2017/06176
See application file for complete search history.

(56) References Cited

U.S. PATENT DOCUMENTS

| 4,187,210 A | 2/1980 | Howard, Jr. |
| 5,037,928 A | 8/1991 | Li et al. |

(Continued)

FOREIGN PATENT DOCUMENTS

WO    WO-9416645    8/1994

OTHER PUBLICATIONS

International Search Report dated Apr. 15, 1994 from PCT Publication PCT/US94/01243.

*Primary Examiner* — Gregory Anderson
(74) *Attorney, Agent, or Firm* — Schwegman Lundberg & Woessner, P.A.

(57) ABSTRACT

A suture passing instrument includes an operation handle, a cannulated needle member, a suture pusher, a suture shuttle and a guide tube. The needle member has a curved end portion. The needle member has an outer sidewall and an inner sidewall defining a bore extending through the needle member for receiving a suture. The suture pusher is movable within the needle member from a retracted position to an extended position. The suture shuttle has at least one bead and is loaded into the bore cannulated needle and movable along the bore by the suture pusher. The guide tube has a body telescopically receiving a retriever loop. The loop is movable between a retracted position and an extended position. A suture can be moved by the suture pusher and captured by the retriever loop.

22 Claims, 12 Drawing Sheets

(52) U.S. Cl.
CPC .............. *A61B 2017/06052* (2013.01); *A61B 2017/06076* (2013.01); *A61B 2017/06176* (2013.01)

(56) References Cited

U.S. PATENT DOCUMENTS

| | | | |
|---|---|---|---|
| 6,102,920 A | 8/2000 | Sullivan et al. | |
| 6,893,448 B2 | 5/2005 | O'Quinn et al. | |
| 7,118,583 B2 | 10/2006 | O'Quinn et al. | |
| 7,232,448 B2 | 6/2007 | Battles et al. | |
| 8,679,135 B2 | 3/2014 | Stone et al. | |
| 2003/0220658 A1 | 11/2003 | Hatch et al. | |
| 2005/0085831 A1 | 4/2005 | Rioux | |
| 2007/0038230 A1 | 2/2007 | Stone et al. | |
| 2008/0091219 A1 | 4/2008 | Marshall et al. | |
| 2009/0018554 A1 | 1/2009 | Thorne et al. | |
| 2010/0114123 A1 | 5/2010 | Nason | |
| 2011/0295279 A1 | 12/2011 | Stone et al. | |
| 2012/0303046 A1 | 11/2012 | Stone et al. | |

METHOD AND APPARATUS FOR PASSING A SUTURE

CROSS-REFERENCE TO RELATED APPLICATIONS

This application is a continuation of U.S. application Ser. No. 13/114,483 filed on May 24, 2011, which claims the benefit of U.S. Provisional Application No. 61/348,016, filed on May 25, 2010. The entire disclosures of the above applications are incorporated herein by reference.

The present application is also related to U.S. patent application Ser. No. 13/114,488 filed on May 24, 2011, the disclosure of which is also incorporated by reference.

FIELD

The present disclosure relates generally to tissue fixation; and more particularly relates to a method and apparatus for passing a suture through tissue.

BACKGROUND

This section provides background information related to the present disclosure which is not necessarily prior art.

In an anatomy, such as a human anatomy, various surgical procedures are often performed to repair or replace various portions thereof. For example, soft tissues of the body may tear or separate from bones due to trauma, overuse, surgical intervention, or disease. These soft tissues can be repaired and/or reattached using sutures or other fastening devices (e.g., screws, staples, or various types of suture anchors).

One means to repair a soft tissue, such as a labral tear, is to thread a suture through a selected portion of the soft tissue. The suture is retrieved from within the surgical site and the free ends of the suture may then be tied together to form a knot. In minimally invasive procedures (e.g., arthroscopic or laparoscopic procedures), however, the surgical site is not readily accessible and the surgeon's ability to thread the suture through the tissue manually is limited. Furthermore, the requisite instruments for retrieving the suture intracorporeally may require an enlarged surgical site.

SUMMARY

This section provides a general summary of the disclosure, and is not a comprehensive disclosure of its full scope or all of its features.

In one form, the present disclosure provides a suture passing instrument including an operation handle, a cannulated needle member, a suture pusher, and a guide tube. The operation handle can have an actuator movable between a first position and a second position. The cannulated needle member can extend from the operation handle and have a curved end portion. The cannulated needle member can have an outer sidewall and an inner sidewall defining a bore extending through the needle member for receiving a suture. The suture pusher can be movable within the needle member from a pusher retracted position to a pusher extended position. The guide tube can have a guide tube body adapted to telescopically receive a retriever loop at a distal end thereof. The retriever loop can be movable between a loop retracted position and a loop extended position. Upon moving the suture pusher from the pusher retracted position to the pusher extended position a suture can be moved by the suture pusher. Upon moving the retriever loop from a loop retracted position to a loop extended position the suture can be captured by the retriever loop.

In another form, the present disclosure provides a method for passing a suture through a tissue with a suture passing instrument having a cannulated needle member and a guide tube. The method can include loading a suture shuttle relative to the cannulated needle member. The method can also include inserting a curved end portion of the cannulated needle member through the tissue. An operation handle can then be rotated, while advancing the needle member through the tissue. The method can also include moving a retriever loop over the curved end portion of the needle member. A suture pusher located within the needle member can then be extended to move the suture from the needle member and capture the suture with the retriever loop. The method can then include retracting the retriever loop to pull the suture through the tissue. The needle member can then be removed from the tissue.

In another form, the present disclosure provides another suture passing instrument including an operation handle, a cannulated needle member, a suture pusher, a guide tube, and a suture shuttle. The operation handle can have at least one actuator movable between a first position and a second position. The cannulated needle member can extend from the operation handle and have a helical end portion. The cannulated needle member can have an outer sidewall and an inner sidewall defining a bore extending through the needle member for receiving a suture. The suture pusher can be movable within the cannulated needle member from a pusher retracted position when the actuator is in the first position to a pusher extended position when the actuator is in the second position. The guide tube can have a guide tube body adapted to movably receive a guide tube extension member. The guide tube extension member can telescopically receive a retriever loop at a distal end thereof. The guide tube extension member can be formed from a rigid material for guiding placement of the retriever loop between a loop retracted position when the actuator is in the first position and a loop extended position when the actuator is in the second position. The retriever loop is compressed when in the loop retracted position and biased open when in the loop extended position. The suture shuttle can be coupled to the suture. Upon moving the actuator from the first position to the second position, the suture shuttle can be moved by the suture pusher and captured by the retriever loop.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
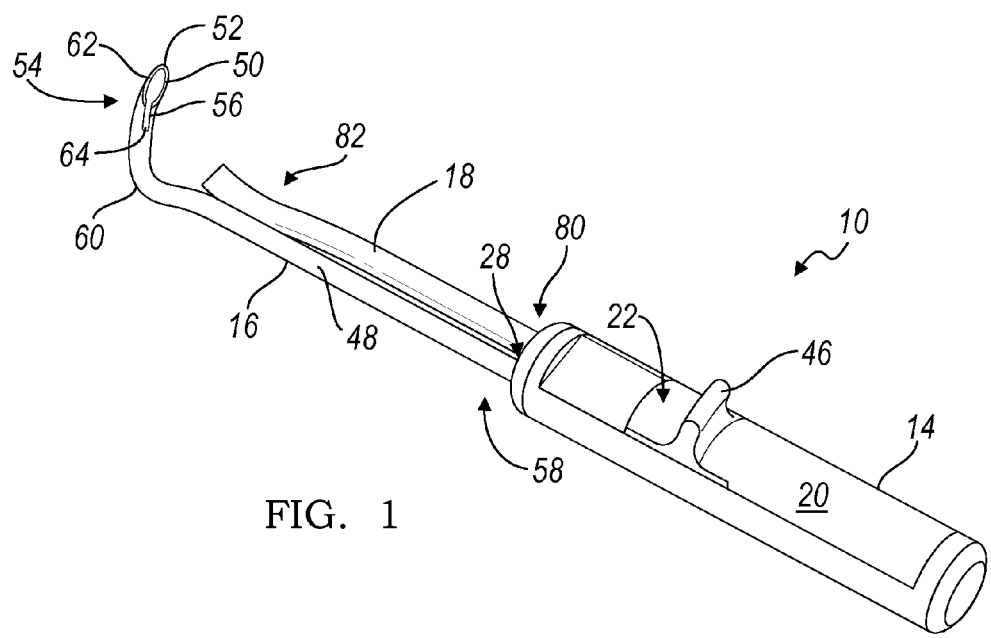
FIG. 1 is a perspective view of a right-helix suture passing instrument constructed in accordance with the teachings of the present disclosure.

The following description of various embodiments is merely exemplary in nature and is not intended to limit the present disclosure, its application, or uses. It should be understood that throughout the drawings, corresponding reference numerals indicate like or corresponding parts and features. With reference to FIGS. 1-20, various methods and apparatuses are disclosed according to the present teachings for passing a suture through an exemplary soft tissue, such as a labrum 88 (FIG. 4A) within a glenohumeral joint, T. However, the various apparatuses and methods may also be used for a plurality of procedures and to repair other soft tissues in the anatomy, such as those damaged through trauma, overuse, surgical intervention, or disease. Therefore, the various apparatuses and methods should not be limited to use only for tissue damage in the glenohumeral area. For example, the various instruments may be used to affix or hold a hamstring, Achilles tendon allograft, other soft tissue, or any other appropriate portion. In addition, although various embodiments may illustrate a suture knot for securing a selected tissue, it will be understood that any mode of securing the afflicted tissue may be used. Therefore, it will be understood that the following discussions are not intended to limit the scope of the present teachings or claims herein.

Referring now to FIG. 1 of the drawings, a right-helix suture passing instrument is generally indicated by reference number 10. Suture passing instrument 10 may be operable for passing a suture 12 (FIG. 4) through the labrum 88 to assist in repairing the joint. Unless specifically mentioned, the various components of the suture passing instrument 10 are made of a biocompatible material, such as stainless steel, to allow for sterilization using chemicals or autoclaving. It is understood that select components described herein can be made from non-stainless steel materials and therefore those select components may not be suitable for all sterilization techniques due to heat sensitivity or chemical sensitivity of the materials. Moreover, suture passing instrument 10 may be a single-use (i.e., disposable) or may be a standardized instrument that can be fitted with removable and replaceable components.

With particular reference to FIGS. 1, 1A, 1B, 1C, 1D, and 1E the suture passing instrument 10 is shown to include an operation handle 14, an elongated shaft or cannulated needle member 16, and a rigid guide tube 18. The operation handle 14 further includes a handle body 20, an actuator 22 disposed thereon, and a slider mechanism 24 disposed therein. As shown and described, the handle body 20 may include at least one opening 26 at a distal end 28 for receiving the needle member 16 and the guide tube 18, a central cavity 30 for receipt of a first, second, and third slide member 32, 36, 40 and a plurality of curved channels 34, 35 located within the central cavity 30 for receipt of the first and second slide members 32, 36, respectively. A translation member 38 may fixedly join the first and second slide members 32, 36 for concurrent linear movement within the central cavity 30. The first and second slide members 32, 36 may move longitudinally within a pair of openings 37, 39 defined by the third slide member 40, while following the curved channels 34, 35 of the central cavity 30. In particular, the first and second slide members 32, 36 are engaged by extending ledges 41, 43 within the pair of openings 37, 39, respectively. The third slide mechanism 40 may be sized to allow only linear movement within the central cavity 30 and may be fixedly secured to the actuator 22 for direct movement therewith. Furthermore, the handle body 20 may be formed from any biocompatible material (e.g., metal or polymer) and may also include a textured exterior surface 42 (e.g., knurl, padding) to provide comfort and/or grip for the operator.

Figure 1A:
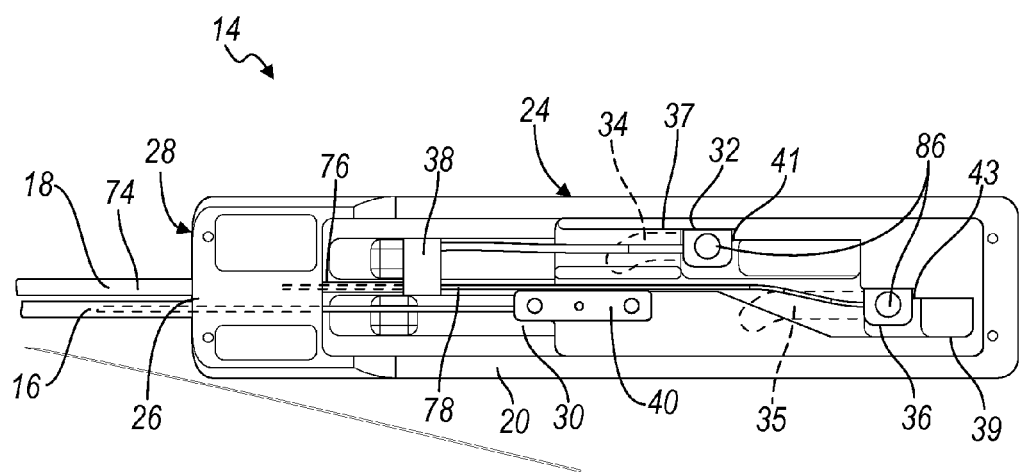
FIG. 1A is a sectional view of an operation handle for the suture passing instrument in a retracted position in accordance with the teachings of the present disclosure.
Figure 1B:
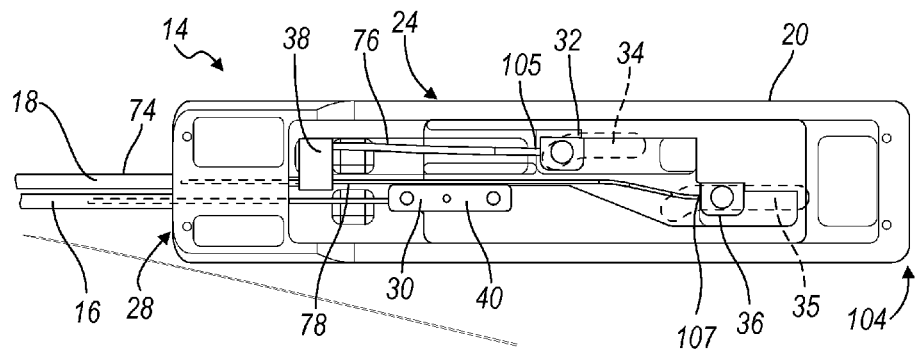
FIG. 1B is a sectional view of an operation handle for the suture passing instrument in an extended position in accordance with the teachings of the present disclosure.
Figure 1C:
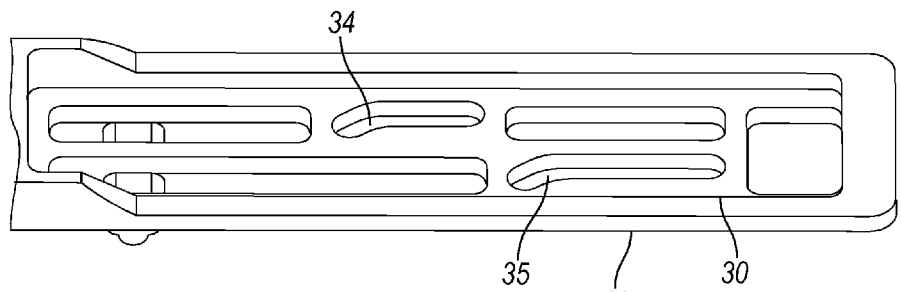
FIG. 1C is a perspective view of the operation handle omitting all inner moving parts.
Figure 1D:
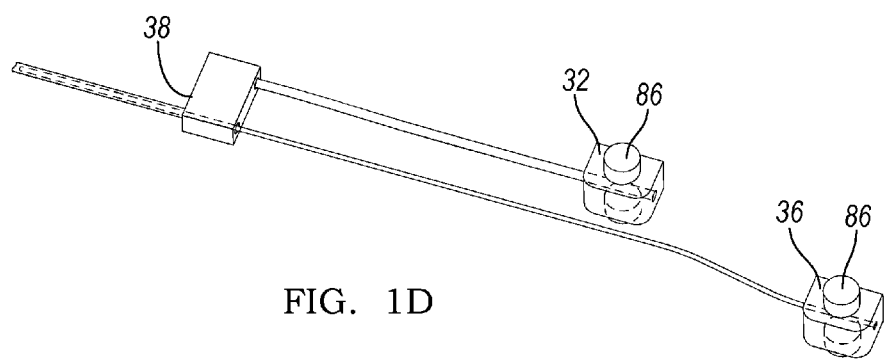
FIG. 1D is a perspective view of a first and second slide mechanism of the operation handle.
Figure 1E:
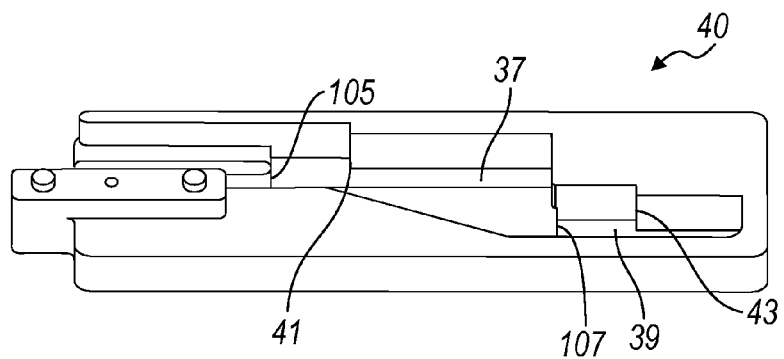
FIG. 1E is a perspective view of a third slide mechanism of the operation handle.
Figure 11:
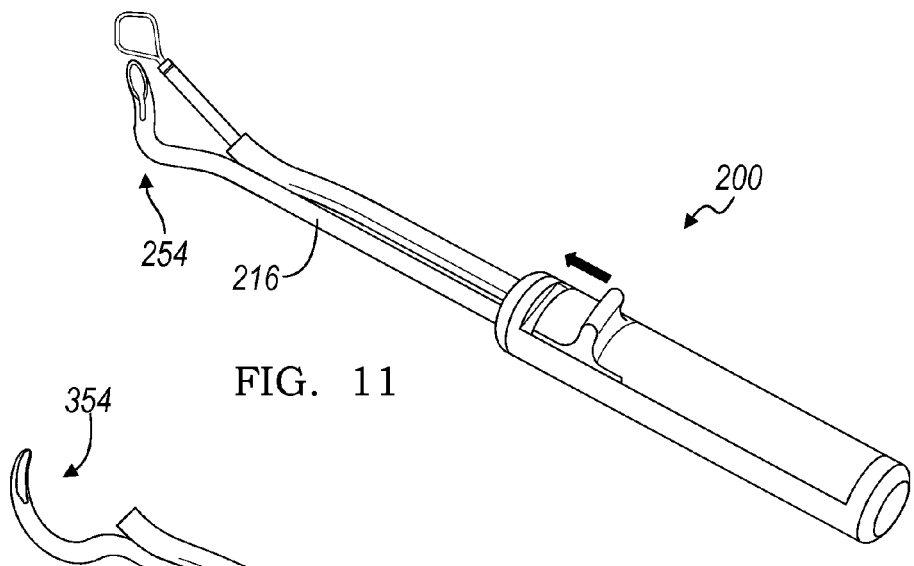
FIG. 11 is a perspective view of a left-helix suture passing instrument in association with a handle member.

As shown and described, the actuator 22 may be one or more trigger members operable for actuating at least the slider mechanism 24 in a longitudinal movement along the handle body 20 from a first or retracted position (as shown in FIGS. 1 and 1A) to a second or extended position (as shown in FIGS. 11 and 1B). It is also contemplated that the actuator 22 may include multiple members 44 moving in tandem or moving independently (e.g., as shown in phantom in FIG. 12). The actuator 22 may define a centrally-raised, finger grip portion 46 for assisting an operator in movement between the retracted and extended positions. Although not shown, the actuator 22 may also incorporate the textured exterior surface (e.g., knurl, padding) to provide comfort and/or grip for the operator.

Figure 2:
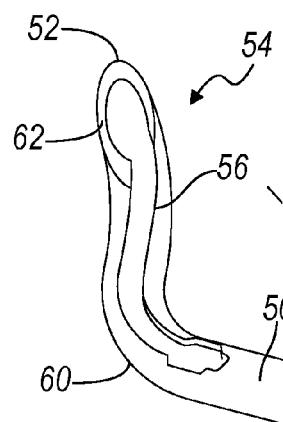
FIG. 2 is an isometric view of the suture passing instrument of FIG. 1.

With reference now to FIGS. 1 and 2, the straight, cannulated needle member 16 and guide tube 18 may extend from the distal end 28 of the handle body 20. The guide tube 18 may be positioned parallel and adjacent to the cannulated needle member 16. The cannulated needle member 16 and guide tube 18 may be fixedly coupled to both the operation handle 14 and to each other in the parallel relationship to prevent relative movement therebetween. The cannulated needle member 16 and guide tube 18 may be fixedly coupled with any known device. As a non-limiting example, the cannulated needle member 16 and guide tube 18 may have a connection member (not shown) located therebetween.

The cannulated needle member 16 may include an elongated, tubular shaft 48 defining an exterior wall 50, a pointed tip 52 located at a distal end 54 of the shaft 48, and a recess or slot 56 in the exterior wall 50 extending from the pointed tip 52. The elongated shaft 48 may have a proximal end 58 extending from the distal end 28 of the handle body 20 and the distal end 54 terminating at the pointed tip 52. At least one bend or curve 60 may be generally located near the distal end 54 of the elongated shaft 48 and may exhibit a "pig-tail" shape or right helix curve over its length. The distal end 54 of the shaft 48 may be rotated to locate an end face 62 parallel to an axis, Y, of the guide tube 18.

Figure 3:
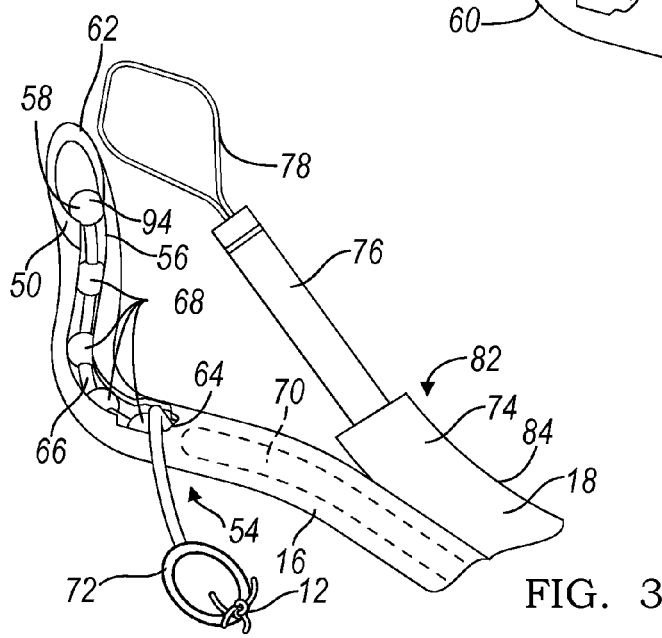
FIG. 3 is a perspective view of the suture passing instrument of FIG. 1 in a suture shuttle load position.

Referring now to FIG. 3, the slot 56 may begin at the end face 62 and extend through the exterior wall 50 of the elongated shaft 48 for a predetermined distance to a widened slot end 64. The slot end 64 may be sized to allow a suture shuttle 66 to be loaded transversely into the cannulated needle member 16 towards the end face 62, but not slip out of the narrowed slot 56. The suture shuttle 66 may include at least one knot or bead 68, which may provide a filler and/or stiffness for engagement with a suture pusher 70 and may also provide an engageable means for retrieving the suture 12, as will be described in more detail with reference to FIG. 7 below. In other words, the slot 56 provides clearance for the suture 12, but not for any of the beads 68 that are loaded through the slot end 64.

The beads 68 of the suture shuttle 66 may be any device known in the art for providing a biocompatible and engageable means for the suture 12. As non-limiting examples, the beads 68 may be shaped nitinol balls crimped onto the suture 12 or connected via a shrink tube. Furthermore, the suture shuttle 66 may include any known suture material (e.g., a polymer material) or any other deformable material (e.g., a metal). Additionally, the suture shuttle 66 may have a retaining loop 72 at an end opposite the beads 68. The retaining loop 72 may fixedly hold the suture 12 during operation of the suture passing instrument 10. In other words, the suture 12 is captured by way of the suture shuttle 66. Notably, however, the retaining loop 72 may be any other device for retaining the suture 12 (e.g., a hook, a jaw, a grasper, etc.).

With continued reference to FIGS. 1 and 3, guide tube 18 may define a guide tube body 74, a guide tube extension member 76 telescopically received therein, and a retriever kite 78 retained within the guide tube extension member 76. The body 74 may have a first, proximal end 80 extending from the distal end 28 of the handle body 20 and a second, distal end 82 terminating near the distal end 54 of the shaft 48. The distal end 82 may incorporate a slight bend 84 so as to bring the retriever kite 78 into alignment with the end face 62 of the cannulated needle member 16. The guide tube extension member 76 may be retained within the guide tube body 74 and may be coupled to or in communication with both the actuator 22 and the retriever kite 78. Therefore, movement of actuator 22 causes movement of the guide tube extension member 76 and the retriever kite 78, as will be described in more detail below.

Retriever kite 78 may be shape set into a predetermined shape, (e.g., a substantially diamond-shaped ring) from a flexible shape memory alloy (e.g., nitinol). In this way, the retriever kite 78 may be retained within the guide tube extension member 76 in one arrangement, but may be deployable into the final diamond-shaped arrangement. Furthermore, the guide tube extension member 76 functions to add rigidity, as well as to accurately place the retriever kite 78 over the pointed tip 52 of the needle member 16, when the retriever kite 78 is in its extended position, while not interfering with the tip 52 or tissue, T, when in its retracted position. In other words, the guide tube extension member 76 positions the retriever kite 78 so that it is aligned with the trajectory of the suture shuttle 66 as it is ejected from the cannulated needle member 16.

As can be seen from FIGS. 1 through 3, the retriever kite 78 may extend through the guide tube extension member 76 and the guide tube body 74 for direct connection with the second slide member 36 in the operation handle 14. The translation member 38 may be fixedly attached to the guide tube extension member 76, while also being rigidly interconnected with the first slide member 32. The translation member 38 may also extend over the retriever kite 78 in the operation handle 14 allowing the retriever kite 78 to move freely of the guide tube extension member 38. Furthermore, the third slide member 40 may be fixedly attached to the suture pusher 70.

The first and second slide members 32, 36 may include extending pins 86 received by the curved channels 34, 35. In the retracted position (FIG. 1A), the first, second, and third slide members 32, 36, 40 may be located at a proximal position within the handle body 20. When the actuator 22 moves to the extended position (FIG. 1B), however, the slide members 32, 36, 40 are moved longitudinally toward the distal end 28 of the handle body 20, with the first slide member 32 moving along the curved channel 34 and the second slide member 36 moving along the curved channel 35 (see FIG. 1C). In another words, when the third slide member 40 (see FIG. 1E) moves longitudinally along the central cavity 30, the extending ledges 41, 43 drivingly contact the first and second slide members 32, 36 causing the slide members 32, 36 (see FIG. 1D) to slide along the curved channels 34, 35. The extending pins 86 of the first and second slide members 32, 36 extend into the curved channels 34, 35 directing the movement of the slide members 32. Notably, the curved channel 34 has a shorter length than the curved channel 35, causing the first slide member 32 to reach the end of the curved channel 34 and slide out of engagement with the extending ledge 41 before the second slide member 36 reaches the end of the curved channel 35. As the second slide member 36 moves towards the distal end 28 of the handle body 20, the extending pin 86, likewise, curves the second slide member 36 away from engagement with the extending ledge 43, removing the associated longitudinal translation force. Notably, however, the actuator 22 continues to move the third slide member 40 and, in turn, the suture pusher 70 towards the distal end 28 of the handle body 20.

Operation of the suture passing instrument 10 will now be described with reference to the labrum 88 of the glenohumeral joint, T, shown in FIGS. 4-10 and the slider mechanism 24 shown in FIGS. 1A and 1B. The labrum 88 is depicted in detail in FIG. 4A as it is within the glenohumeral joint, T, but it is obstructed from view in the other figures in order to shown positioning of the helix in the tissue. It should be understood, however, that the repair as described herein is being completed on the labrum 88. Initially with the actuator 22 in the retracted position, the suture shuttle 66 is loaded into the slot 56 in the cannulated needle member 16 through the widened slot end 64. The suture shuttle 66 may be loaded into the slot 56 with a first bead 94 entering the widened slot end 64 and moving distally towards the end face 62. Once all beads 68 have been inserted into the tubular shaft 48, they may terminate near the pointed tip 52 with the suture 12 extending from the slot end 64 (FIG. 3).

Figure 4:
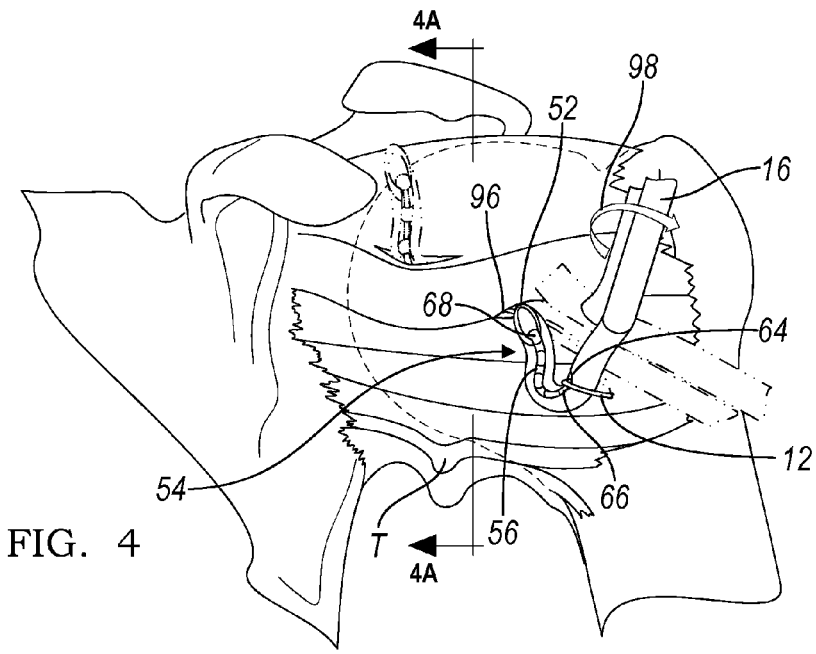
FIG. 4 is a perspective view of the suture passing instrument of FIG. 1 in an initial operative position in association with a labrum tear within a glenohumeral joint.
Figure 4A:
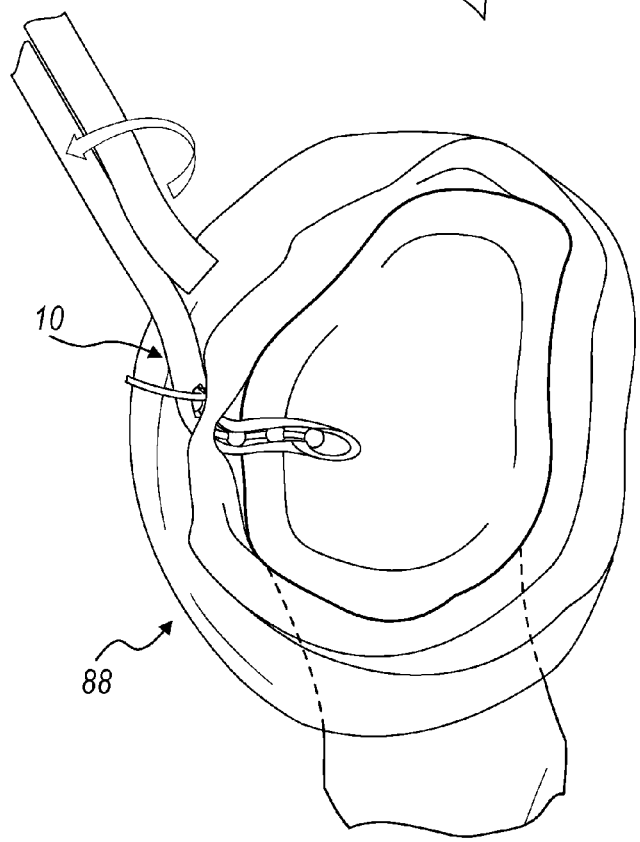
FIG. 4A is a sectional view of the labrum tear of FIG. 4 taken through section 4A-4A.

With particular reference to FIG. 4, the pointed tip 52 of the distal end 54 is brought into contact with the labrum 88 of the glenohumeral joint, T, with no rotational movement. The sharpened point of the tip 52 pierces the ligament, T, and allows the suture passing instrument 10 to establish an opening 96 within the labrum 88 within the joint, T. As the suture passing instrument 10 is inserted through the opening 96, the operation handle 14 is rotated in a counter-clockwise manner, as shown by rotational arrow 98, in order to maintain a minimal size for the opening 96. The operation handle 14 may be rotated anywhere between approximately one-quarter of a turn to one full revolution to extend the cannulated needle member 16 out of the ligament, T. The amount of rotation for the operation handle 14 may depend upon the dimensional shape of the curve 60 of the distal end 54. The final orientation of the distal end 54 is shown in phantom.

Figure 5:
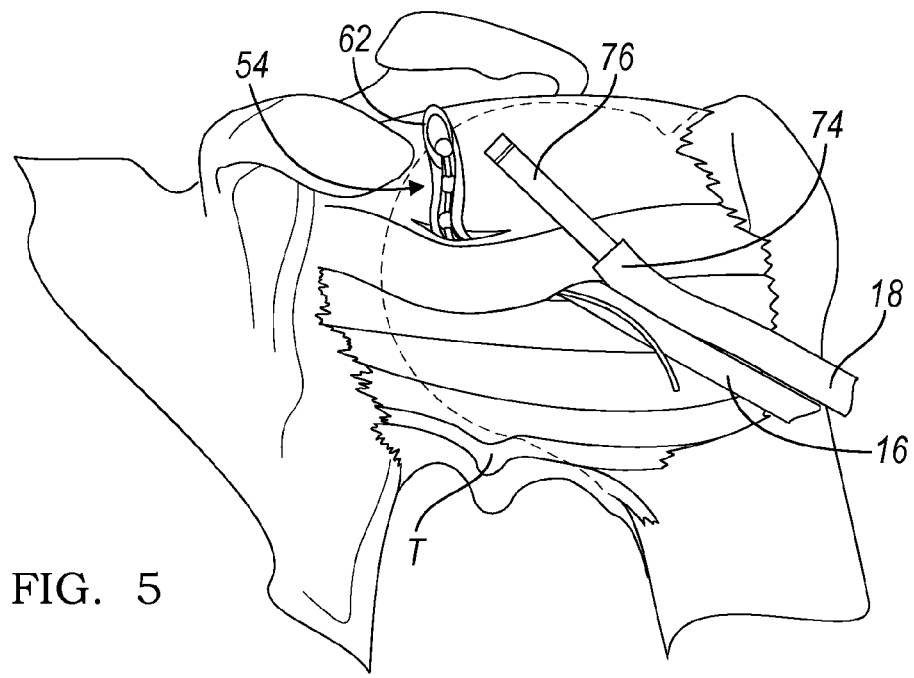
FIG. 5 is a perspective view of the suture passing instrument of FIG. 1 in an intermediate operative position depicting a guide tube advanced toward a needle tip.

Referring now to FIGS. 1A, 1B, and 5, after the distal end 54 of the cannulated needle member 16 is fully and thoroughly inserted into the ligament, T, the actuator 22 begins movement to the extended position. The actuator 22 is fixedly attached to the slider mechanism 24, so that longitudinal movement of the actuator 22 to the extended position, in turn, causes movement of the slider mechanism 24. In particular, the actuator 22 drives the third slide member 40 towards the distal end 28 of the handle body 20. This longitudinal movement causes the first and second slide members 32, 36 to translate in the openings 37, 39 by engagement with the extending ledges 41, 43 of the third slide member 40. The extending pins 86 of the first and second slide members 32, 36 follow the curved channels 34, 35 and the central cavity 30, respectively. As previously described, the translation movement of the first and second slide members 32, 36 cause the guide tube extension member 76 and the retriever kite 78 to extend through the guide tube body 74 at an equivalent speed. Concurrently, the third slide member 40 is driven longitudinally by the actuator 22 causing the suture pusher 70 to extend through and out of the cannulated needle member 16. Accordingly, the guide tube extension member 76 moves distally out of the guide tube body 74 towards the end face 62 of the cannulated needle member 16.

As the first slide member 32 reaches the end of the curved channel 34, the extending pin 86 moves the slide member 32 out of alignment with the extending ledge 41 of the third slide member 40. The length of the curved channel 34 allows the guide tube extension member 76 to extend out of the guide tube body 74 by a predetermined distance. Accordingly, as the driving force of the actuator 22 is removed from the first slide member 32 the guide tube extension member 76 ceases longitudinal movement.

Figure 6:
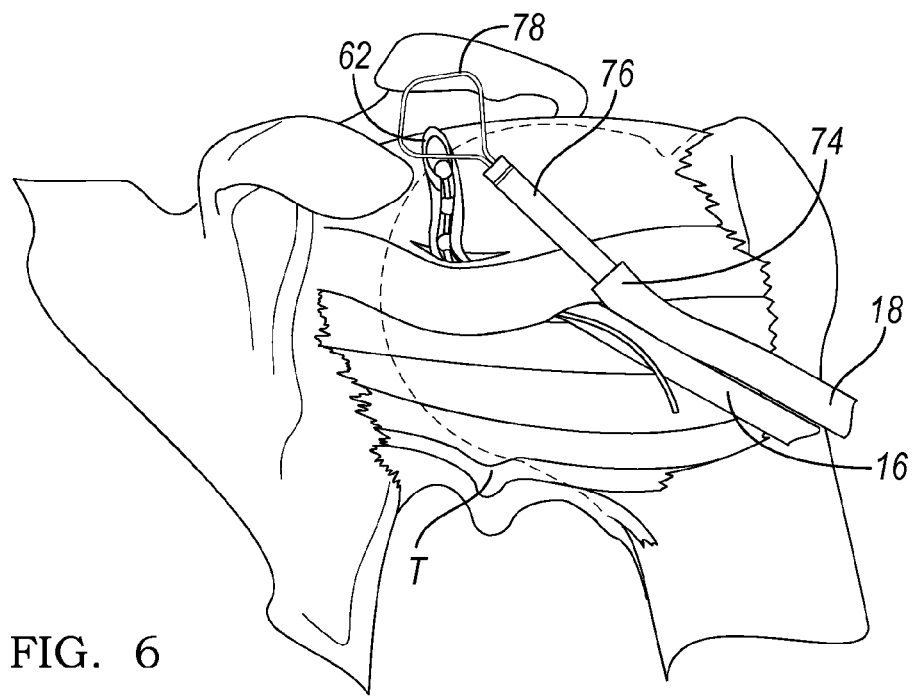
FIG. 6 is a perspective view of the suture passing instrument of FIG. 1 in an intermediate operative position depicting deployment of a retriever loop.

With reference now to FIGS. 1A, 1B, and 6, the second slide member 36 continues its longitudinal translation through the curved channel 35 in the central cavity 30, extending the retriever kite 78 as it moves. As should be understood, the retriever kite 78 continues movement with the second slide member 36, which causes its extension from the guide tube extension member 76 and the guide tube body 74. In this motion, the retriever kite 78 opens from a collapsed condition and extends outwardly from the guide tube extension member 76 and over the end face 62 of the cannulated needle member 16.

Once the second slide member 36 reaches the end of the curved channel 35, the extending pin 86 of the second slide member 36 also curves the slide member 36 away from alignment with the extending ledge 43 of the third slide member 40, removing its longitudinal driving force. The length of the curved channel 35 allows the retriever kite 78 to extend out of the guide tube extension member 76 by a predetermined distance. Accordingly, as the driving force of the actuator 22 is removed from the second slide member 36 the retriever kite 78 also ceases longitudinal movement.

Figure 7:
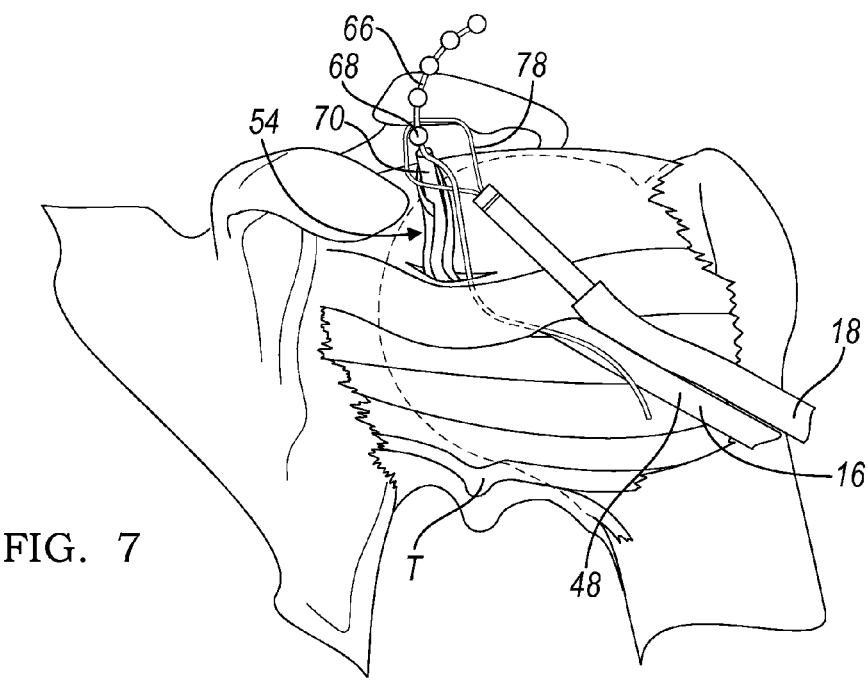
FIG. 7 is a perspective view of the suture passing instrument of FIG. 1 in an intermediate operative position depicting a shuttle pusher advancing the suture shuttle from the needle tip.

Referring now to FIGS. 1A, 1B, and 7, once the retriever kite 78 is located over the end face 62 of the needle member 16, the actuator 22 directly advances the suture pusher 70 through the elongated shaft 48. In other words, the actuator 22 is directly coupled to the third slide member 40, which is fixedly secured to the suture pusher 70 for axial translation of the suture pusher 70. The actuator 22 may continue longitudinal movement of the third slide member 40 until the translation member 38 contacts the distal end 28 of the handle body 20. Once translated, the beads 68 of the suture shuttle 66 are engaged by the suture pusher 70 to force the suture shuttle 66 out of the distal end 54 of the needle member 16. Thereafter, the suture shuttle 66 is pushed through the deployed retriever kite 78.

Figure 8:
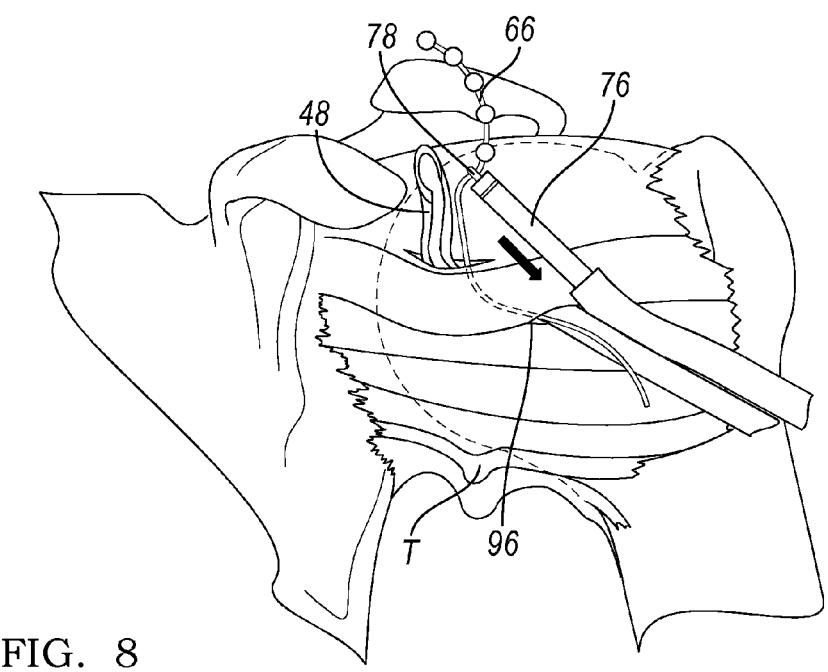
FIG. 8 is a perspective view of the suture passing instrument of FIG. 1 in an intermediate operative position depicting the retriever loop capturing the suture shuttle.

Referring now to FIGS. 1A, 1B, and 8, after the suture 12 extends through the deployed retriever kite 78, the operator may then return the actuator 22 to the retracted position. The suture pusher 70 returns to its initial position within the elongated shaft 48, by translating the third slide member 40 within the central cavity 30. The retriever kite 78 collapses as it is retracted into the guide tube extension member 76. As the retriever kite 78 collapses, it captures the suture shuttle 66. It should be understood, however, that the retriever kite 78 might not fully retract into the guide tube extension member 76 as the capture of the suture shuttle 66 may prevent complete retraction.

Figure 9:
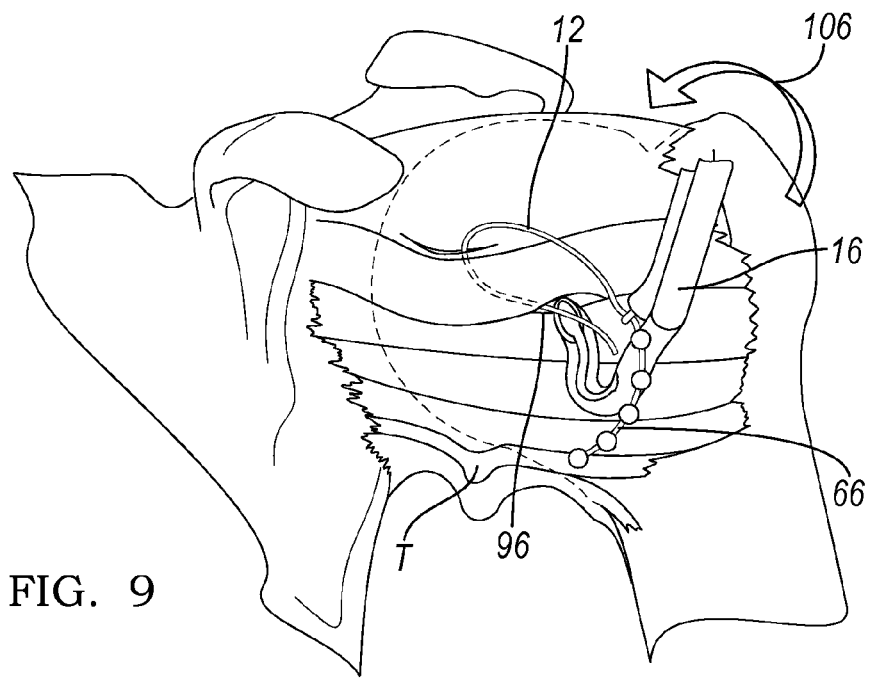
FIG. 9 is a perspective view of the suture passing instrument of FIG. 1 in a final retracted position and being removed from the glenohumeral tissue.

With reference now to FIGS. 1A, 1B, and 9, the retraction of the actuator 22 applies a reverse longitudinal force to the slider mechanism 24. In particular, the actuator 22 drives the slider mechanism 24 towards a proximal end 104 of the handle body 20. The longitudinal movement of the actuator 22 drives the third slide member 40 towards the proximal end 104 of the handle body 20. The third slide member 40 engages the first and second slide members 32, 36 with stop surfaces 105, 107 causing the first and second slide members 32, 36 to translate in a reverse direction along the curved channels 34, 35. The concurrent movement of the first and second slide members 32, 36 causes the guide tube extension member 76 and the retriever kite 78 to retract into the guide tube body 74. Notably, the suture shuttle 66 prevents the suture 12 from sliding out of the retracted retriever kite 78. The cannulated needle member 16 may then be withdrawn from the ligament, T. Withdrawal of the cannulated needle member 16 is accomplished in reverse of insertion (i.e., rotation occurs in a clockwise motion), as shown by rotational arrow 106, with the needle member 16 being removed from the ligament, T, at the opening 96.

Figure 10:
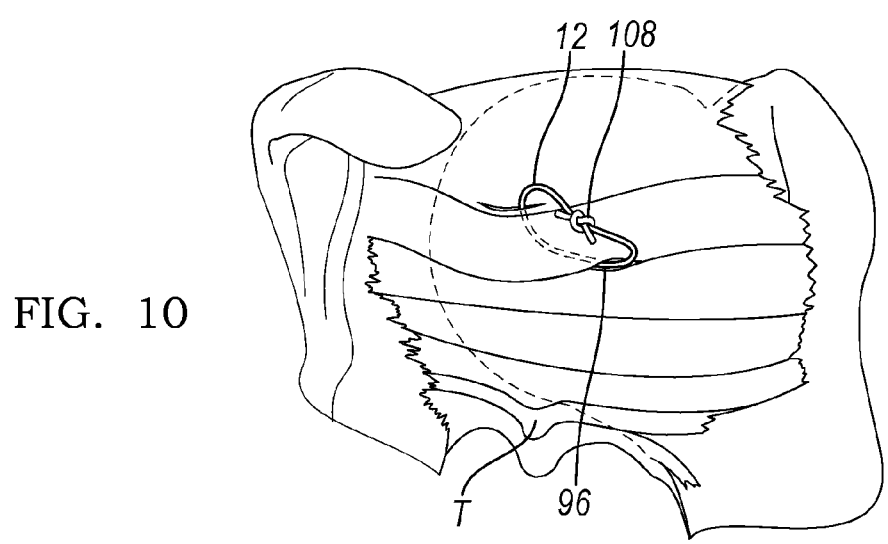
FIG. 10 is a perspective view of the glenohumeral tissue after removal of the suture passing instrument and securement of the suture.

Referring now to FIG. 10, the suture passing instrument 10 is removed from the surgical site. After this motion is complete, the suture 12 will be threaded through the opening 96 within the glenohumeral ligament, T. The suture shuttle 66 can then be removed from the suture 12 and the ends of the suture 12 can then be knotted 108 outside of the surgical opening for a minimally invasive repair.

With reference now to FIG. 11, an alternative suture passing instrument 200 is shown. Suture passing instrument 200 is also operable for passing the suture 12 through the labrum 88 to assist in repairing the joint, as previously described with respect to suture passing instrument 10. Furthermore, many of the components of suture passing instrument 10 remain unchanged in suture passing instrument 200. For example, suture passing instrument 200 uses a similar operation handle 14 and guide tube 18. Suture passing instrument 200, however, exhibits a left helix curve at a distal end 254 of a needle member 216, instead of the right helix curve described with respect to the suture passing instrument 10. Accordingly, during insertion of the suture passing instrument 200, the operation handle 14 must be rotated in a clockwise manner in order to maintain the minimal size for the opening 96. While suture passing instrument 10 and suture passing instrument 200 are highly similar, certain surgeons may prefer one design to the other due to right- or left-hand dominance or for other reasons not articulated herein.

Figure 12:
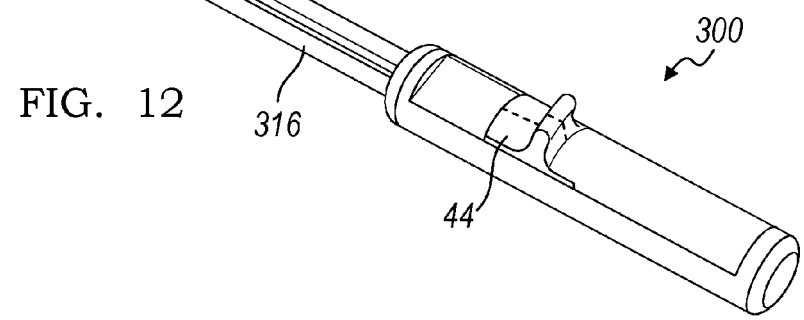
FIG. 12 is a perspective view of a linear curve suture passing instrument in association with a handle member.

Referring now to FIG. 12, another alternative suture passing instrument 300 is shown. Suture passing instrument 300 is also operable for passing the suture 12 through the labrum 88 to assist in repairing the joint, as previously described with respect to suture passing instrument 10. Furthermore, many of the components of suture passing instrument 10 remain unchanged in suture passing instrument 300. For example, suture passing instrument 300 uses a similar operation handle 14 and guide tube 18. Suture passing instrument 300, however, exhibits a linear curve (i.e., "ice cream scoop") at an end 354 of a needle member 316, instead of the right helix curve at the distal end 54 described with respect to the suture passing instrument 10. Accordingly, during insertion of the suture passing instrument 300, the operation handle 14 need only to be moved in a single plane in order to maintain the minimal size for the opening 96. While suture passing instrument 10 and suture passing instrument 300 are highly similar, certain surgeons may prefer one design to the other due to space considerations or for other reasons not articulated herein.

Figure 13:
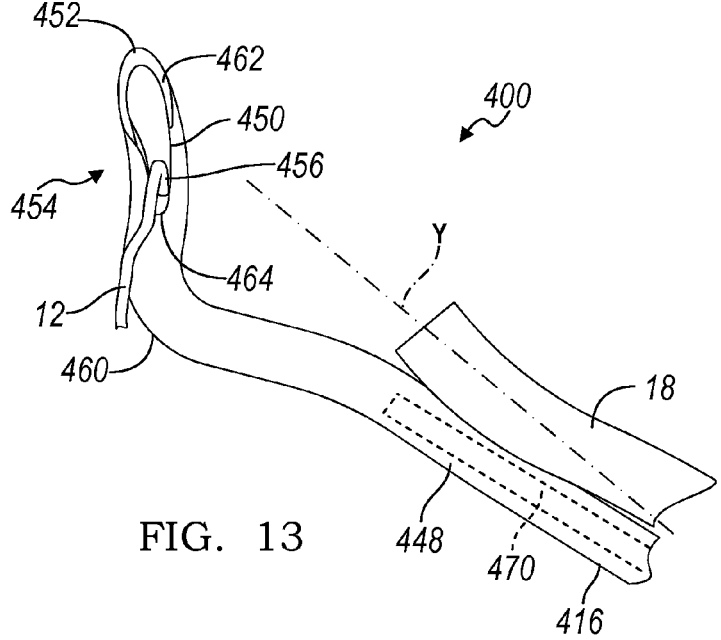
FIG. 13 is a perspective view of an alternate suture passing instrument in a suture shuttle load position.

With reference now to FIG. 13, yet another alternative suture passing instrument 400 is shown. Suture passing instrument 400 is also operable for passing the suture 12 through the labrum 88 of the glenohumeral joint, T, to assist in repairing the tissue, as previously described with respect to suture passing instrument 10. Furthermore, suture passing instrument 400 uses a similar operation handle 14, guide tube 18, and suture shuttle 66, which is not shown and will not be described in detail herein. However, suture passing instrument 400 includes a cannulated needle member 416 extending from the distal end 28 of the operation handle 14 having an alternately designed distal end 454. Both the needle member 416 and guide tube 18 may be fixedly coupled to the operation handle 14 and maintain a parallel relationship for preventing relative movement therebetween.

The needle member 416 may include an elongated, tubular shaft 448 defining an exterior wall 450, a pointed tip 452 located at a distal end 454 of the elongated shaft 448, and a notch 456 in the exterior wall 450 extending from the pointed tip 452. Notably, the notch 456 is much narrower and shallow than the slot 56 of the cannulated needle member 16. Accordingly, the overall strength and integrity of cannulated needle member 416 is improved over that of the cannulated needle member 16. Although not shown, it should be understood that the notch 456 may also be completely omitted from the cannulated needle member 416.

The elongated shaft 448 may extend from the end 28 of the handle body 20 to the distal end 454 terminating at the pointed tip 452. At least one bend or curve 460 may be generally located near the distal end 454 of the elongated shaft 448 and may exhibit a "pig-tail" shape or right helix curve over its length. The distal end 454 of the shaft 448 may be rotated to locate an end face 462 parallel to an axis, Y, of the guide tube 18.

The notch 456 may begin at the end face 462 and extend through the exterior wall 450 of the elongated shaft 448 for a predetermined distance to a slot end 464. The notch 456 may be sized to allow the suture shuttle 66 to be passed through the end face 462 of the pointed tip 452 of the cannulated needle member 416 with the suture 12 extending outwardly at the slot end 464. When the notch 456 is omitted, the suture 12 will not extend out of the slot end 464, bur rather out of the end face 462 of the pointed tip 452 of the cannulated needle member 416. The cannulated needle member 416 may also include a suture pusher 470 within the elongated shaft 448 for engaging the suture shuttle 66, as will be described in more detail with reference to FIG. 18 below.

Operation of the suture passing instrument 400 will now be described with reference to the glenohumeral ligament, T, shown in FIGS. 13-20 and the slider mechanism 24 shown in FIGS. 1A and 1B. Initially with the actuator 22 in the retracted position, the suture shuttle 66 is loaded into the cannulated needle member 416 through the end face 462, beads 68 first, with the suture 12 extending out of the notch 456. Once all beads 68 have been inserted into the tubular shaft 448, they may terminate near the pointed tip 452 with the suture 12 extending from the slot end 464 (FIG. 13).

Figure 14:
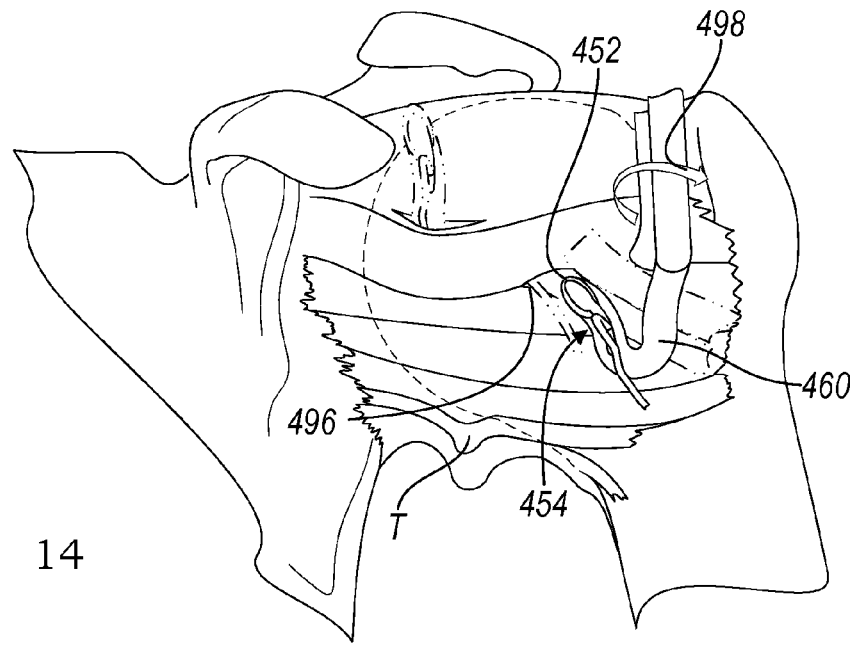
FIG. 14 is a perspective view of the suture passing instrument of FIG. 13 in an initial operative position in association with a glenohumeral tissue.

With particular reference to FIG. 14, the pointed tip 452 of the distal end 454 is brought into contact with the labrum 88 (FIG. 4) of the glenohumeral joint, T, with no rotational movement. The sharpened point of the tip 452 pierces the ligament, T, and allows the suture passing instrument 400 to establish an opening 496 within the ligament, T. As the suture passing instrument 400 is inserted into the opening 496 within the ligament, T, the operation handle 14 is rotated in a counter-clockwise manner, as shown by rotational arrow 498, in order to maintain a minimal size for the opening 496. The operation handle 14 may be rotated anywhere between approximately one-quarter of a turn to one full revolution to extend the cannulated needle member 416 out of the ligament, T. The amount of rotation for the operation handle 14 may depend upon the dimensional shape of the curve 460 at the distal end 454. The final orientation of the distal end 454 is shown in phantom.

Figure 15:
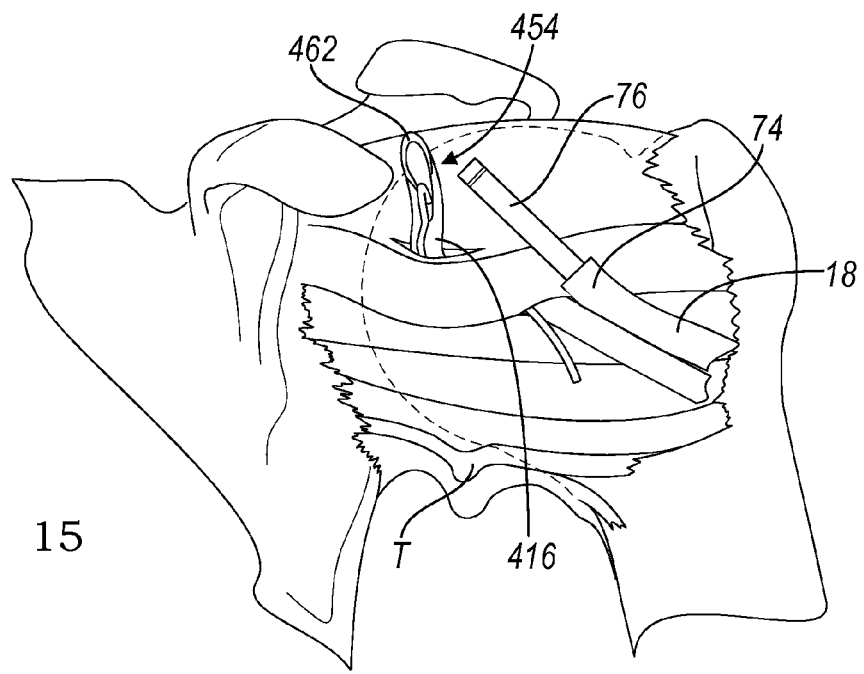
FIG. 15 is a perspective view of the suture passing instrument of FIG. 13 in an intermediate operative position depicting a guide tube advanced toward a needle tip.

Referring now to FIGS. 1A, 1B, and 15, after the distal end 454 of the cannulated needle member 416 is fully and thoroughly inserted into the ligament, T, the actuator 22 is moved to the extended position. The actuator 22 is fixedly attached to the slider mechanism 24, so that longitudinal movement of the actuator 22 to the extended position, in turn, causes movement of the slider mechanism 24. In particular, the actuator 22 drives the third slide member 40 towards the distal end 28 of the handle body 20. This longitudinal movement causes the first and second slide members 32, 36 to translate in the openings 37, 39 by engagement with the extending ledges 41, 43 of the third slide member 40. The extending pins 86 of the first and second slide members 32, 36 follow the curved channels 34, 35 and the central cavity 30, respectively. As previously described, the translation movement of the first and second slide members 32, 36 cause the guide tube extension member 76 and the retriever kite 78 to extend through the guide tube body 74 at an equivalent speed. Concurrently, the third slide member 40 is driven longitudinally by the actuator 22 causing the suture pusher 470 to extend through and out of the cannulated needle member 416. Accordingly, the guide tube extension member 76 of the guide tube 18 moves distally out of the guide tube body 74 towards the end face 462 of the cannulated needle member 416.

As the first slide member 32 reaches the end of the curved channel 34, the extending pin 86 moves the slide member 32 out of alignment with the extending ledge 41 of the third slide member 40. The length of the curved channel 34 allows the guide tube extension member 76 to extend out of the guide tube body 74 by a predetermined distance. Accordingly, as the driving force of the actuator 22 is removed from first slide member 32 the guide tube extension member 76 ceases longitudinal movement.

Figure 16:
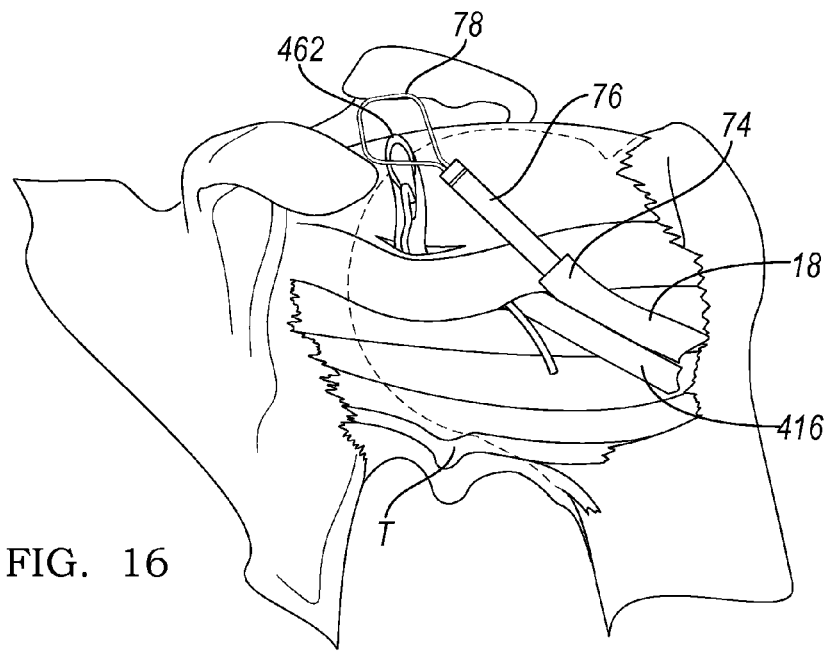
FIG. 16 is a perspective view of the suture passing instrument of FIG. 13 in an intermediate operative position depicting deployment of a retriever loop.

With reference now to FIGS. 1A, 1B, and 16, the second slide member 36 continues its longitudinal translation through the curved channel 35 in the central cavity 30, extending the retriever kite 78 as it moves. As should be understood, the retriever kite 78 continues movement with the second slide member 36, which causes its extension from the guide tube extension member 76 and the guide tube body 74. In this motion, the retriever kite 78 extends outwardly from the guide tube extension member 76 and over the end face 462 of the cannulated needle member 416.

Once the second slide member 36 reaches the end of the curved channel 35, the extending pin 86 of the second slide member 36 also curves the slide member 36 away from alignment with the extending ledge 43 of the third slide member 40, removing its longitudinal driving force. The length of the curved channel 35 allows the retriever kite 78 to extend out of the guide tube extension member 76 by a predetermined distance. Accordingly, as the driving force of the actuator 22 is removed from the second slide member 36 the retriever kite 78 also ceases longitudinal movement.

Figure 17:
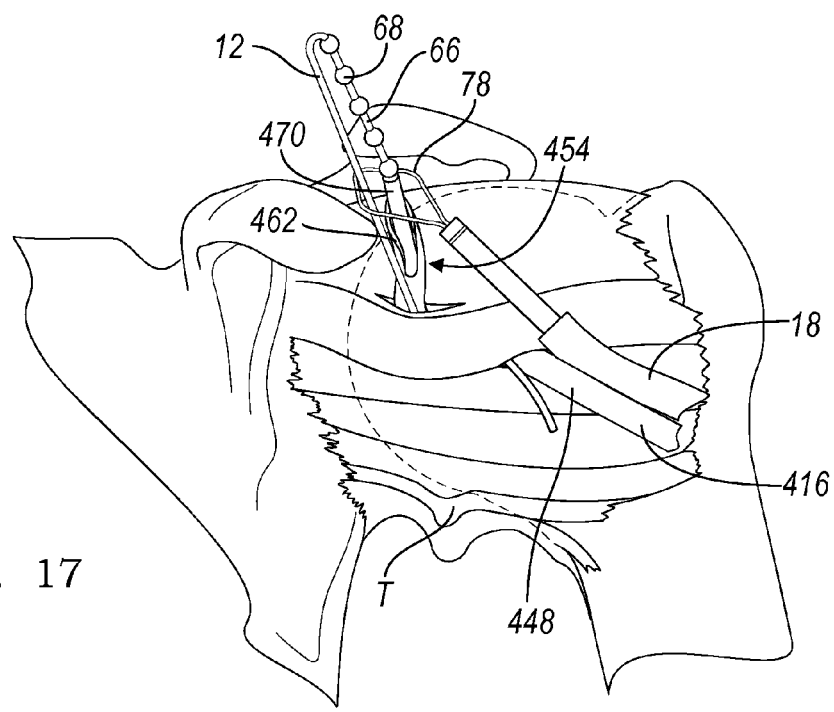
FIG. 17 is a perspective view of the suture passing instrument of FIG. 13 in an intermediate operative position depicting a shuttle pusher advancing the suture shuttle from the needle tip.

Referring now to FIGS. 1A, 1B, and 17, once the retriever kite 78 is located over the end face 462 of the needle member 416, the actuator 22 directly advances the suture pusher 470 through the elongated shaft 448, engaging the beads 68 of the suture shuttle 66 and forcing it out of the distal end 454 of the needle member 416. In other words, the actuator 22 is directly coupled to the third slide member 40, which is fixedly secured to the suture pusher 470 to axially translate the suture pusher 470. The suture shuttle 66 is pushed through the deployed retriever kite 78.

Figure 18:
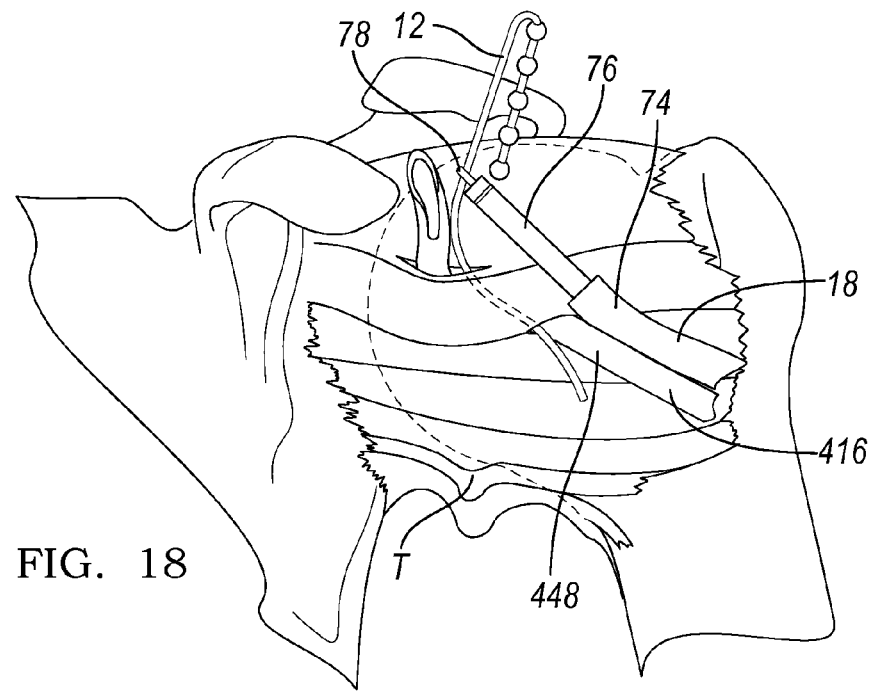
FIG. 18 is a perspective view of the suture passing instrument of FIG. 13 in an intermediate operative position depicting the retriever loop capturing the suture shuttle.

Referring now to FIGS. 1A, 1B, and 18, after both the suture shuttle 66 and the suture 12 extend through the deployed retriever kite 78, the operator may then return the actuator 22 to the retracted position. The suture pusher 470 returns to its initial position within the elongated shaft 448 by translating the third slide member 40 within the central cavity 30. The retriever kite 78 is retracted into the guide tube extension member 76. It should be understood, however, that the retriever kite 78 might not fully retract into the guide tube extension member 76 as the capture of the suture shuttle 66 may prevent complete retraction. Notably, the suture shuttle 66 prevents the suture 12 from sliding out of the retracted retriever kite 78.

Figure 19:
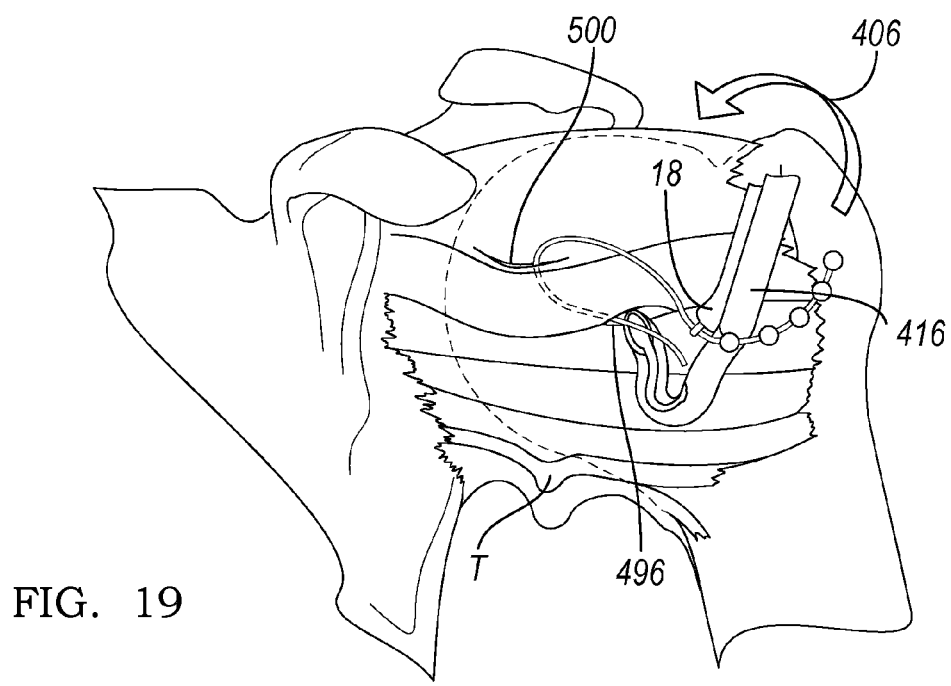
FIG. 19 is a perspective view of the suture passing instrument of FIG. 13 in a final retracted position and being removed from the glenohumeral tissue.

With reference now to FIGS. 1A, 1B, and 19, the retraction of the actuator 22 applies a reverse longitudinal force to the slider mechanism 24. In particular, the actuator 22 drives the slider mechanism 24 towards the proximal end 104 of the handle body 20. The longitudinal movement of the actuator 22 drives the third slide member 40 towards the proximal end 104 of the handle body 20. The third slide member 40 engages the first and second slide members 32, 36 with stop surfaces 105, 107 causing the first and second slide members 32, 36 to translate in a reverse direction along the curved channels 34, 35. The concurrent movement of the first and second slide members 32, 36 causes the guide tube extension member 76 and the retriever kite 78 to retract into the guide tube body 74. Notably, the suture shuttle 66 prevents the suture 12 from sliding out of the retracted retriever kite 78. The cannulated needle member 416 may then be withdrawn from the ligament, T. Withdrawal of the cannulated needle member 416 is accomplished in reverse of insertion (i.e., rotation occurs in a clockwise motion), as shown by rotational arrow 406 with the needle member 416 being removed from the ligament, T, at the tissue opening 496.

Figure 20:
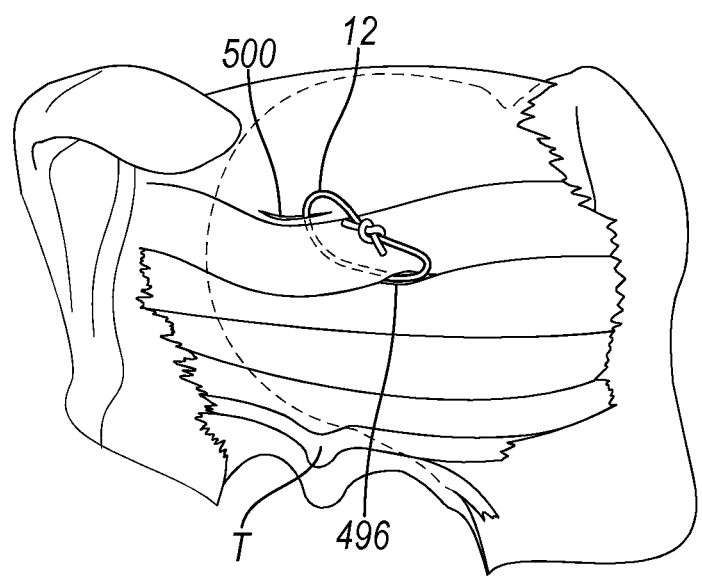
FIG. 20 is a perspective view of the glenohumeral tissue after removal of the suture passing instrument of FIG. 13 and securement of the suture.

Referring now to FIG. 20, the suture passing instrument 400 is removed from the surgical site. After this motion is complete, the suture 12 will be threaded through the opening 496 within the glenohumeral ligament, T. The suture shuttle 66 can then be removed from the suture 12 and the ends of the suture 12 can then be knotted 508 outside of the surgical opening for a minimally invasive repair.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure. In certain embodiments, for example, it may be necessary to immovably secure the needle members and guide tubes. Furthermore, the complete omission of the guide tube extension member and/or the suture shuttle is contemplated. Additionally, the actuator 22 has been described as being movable between two positions; however, the actuator 22 may be movable between any number of positions to enable greater flexibility for the operator, as necessary. Furthermore, the suture passing instruments may incorporate either a removable or integrally formed needle member. The removable needle member may be connected to the elongated shaft through any known means, such as, bayonet slot, threading, or interference fit. Furthermore, the removable needle member may be selected from a plurality of needle members or from a pre-packaged kit.

What is claimed is:
1. A suture passing instrument comprising:
an operation handle having an actuator movable between a first position and a second position;
a cannulated needle member extending from the operation handle and having a curved end portion, the cannulated needle member having an outer sidewall and an inner sidewall defining a bore extending through the needle member for use in delivering a suture;
a suture pusher movable within the needle member from a pusher retracted position to a pusher extended position;
a suture shuttle configured to be loaded into the bore of the cannulated needle and operable to be coupled to the suture, the suture shuttle having at least one bead and movable along the bore by the suture pusher; and a guide tube having a guide tube body adapted to telescopically receive a retriever loop at a distal end thereof, wherein the retriever loop is movable between a loop retracted position and a loop extended position outside the guide tube, wherein upon moving the suture pusher from the pusher retracted position to the pusher extended position, the suture shuttle and the suture can be moved by the suture pusher, and wherein the suture shuttle is configured such that upon moving the retriever loop from a loop retracted position to a loop extended position the suture can be captured by the retriever loop outside the guide tube.

2. The suture passing instrument of claim 1, wherein the curved end portion is one of a right helix curve, a left helix curve, or a linear curve.

3. The suture passing instrument of claim 1, wherein the suture is captured by the retriever loop upon the retriever loop being retracted about the at least one bead.

4. The suture passing instrument of claim 3, wherein the at least one bead is one of a deformable metal and a polymer.

5. The suture passing instrument of claim 3, wherein the suture shuttle defines one of a retaining loop, a hook, a jaw, and a grasper for fixedly securing to the suture.

6. The suture passing instrument of claim 3, wherein the suture pusher engages the suture shuttle when in the pusher extended position.

7. The suture passing instrument of claim 3, wherein the cannulated needle includes an elongated slot extending from an end face of the cannulated needle and communicating with the bore.

8. The suture passing instrument of claim 7, wherein the slot is formed in the curved end portion and extends transversely from the end face for a predetermined length from the inner sidewall to the outer sidewall.

9. The suture passing instrument of claim 7, wherein the slot includes a widened end for transversely receiving the suture shuttle.

10. The suture passing instrument of claim 1, wherein the guide tube body movably receives a guide tube extension member for guiding the retriever loop, the guide tube extension member being formed from a rigid material for guiding placement of the retriever loop.

11. The suture passing instrument of claim 1, wherein the retriever loop is biased open when in the loop extended position.

12. The suture passing instrument of claim 1, wherein the actuator further comprises a first member operable for actuating the suture pusher between the pusher retracted and extended positions, and a second member operable for actuating the retriever loop between the loop retracted and extended positions.

13. The suture passing instrument of claim 1, wherein a slider mechanism is disposed within the operation handle, the slider mechanism further comprising:
   first and second slides axially movable along a pair of corresponding channels defined by the operation handle;
   a third slide axially movable within the operation handle; and
   a translation member in communication with at least one of the first and second slides for moving the retriever loop between the loop retracted and extended positions.

14. A method for passing a suture through a tissue with a suture passing instrument having a cannulated needle member and a guide tube, the method comprising:
   inserting an end portion of the cannulated needle member through the tissue;
   rotating an operation handle while advancing the needle member through the tissue;
   moving a retriever loop through and outside the guide tube over the end portion of the needle member;
   extending a suture pusher located within the cannulated needle member to move a suture shuttle having at least one bead and carrying a suture from the needle member and capture the suture with the retriever loop outside the guide tube;
   retracting the retriever loop to pull the suture through the tissue; and
   removing the needle member from the tissue.

15. The method of claim 14, wherein the bead is a deformable bead.

16. The method of claim 14, further comprising:
   loading the at least one bead into the cannulated needle member through a widened portion of an elongated slot extending transversely from an end face of the cannulated needle member.

17. The method of claim 14, further comprising:
   loading the at least one bead into the cannulated needle member through an end face of the cannulated needle member.

18. The method of claim 14, wherein extending the suture pusher further comprises capturing the suture shuttle with the retriever loop.

19. The method of claim 14; further comprising:
   deploying a guide tube extension member before deploying the retriever loop, wherein the retriever loop is telescopically received within the guide tube extension member and the guide tube extension member is telescopically received within the guide tube.

20. A method for passing a suture through a tissue with a suture passing instrument having a cannulated needle member and a guide tube, the method comprising:
   securing a suture to a suture shuttle having at least one bead;
   loading the suture shuttle into a bore of the cannulated needle member;
   inserting a curved end portion of the cannulated needle member through the tissue;
   advancing the cannulated needle member through the tissue;
   moving a retriever loop through and outside the guide tube over the curved end portion of the needle member;
   extending a suture pusher located within the cannulated needle member to move the suture shuttle and the suture from the needle member and capture the suture with the retriever loop outside the guide tube;
   retracting the retriever loop to pull the suture; and
   removing the needle member from the tissue.

21. The method of claim 20, further comprising:
   passing the at least one bead into the cannulated needle member through an end face of the cannulated needle member.

22. The method of claim 20, further comprising:
   passing the at least one bead into the cannulated needle member through a widened portion of an elongated slot extending transversely from an end face of the cannulated needle member.

* * * * *